(12) United States Patent
Jung et al.

(10) Patent No.: US 10,959,641 B2
(45) Date of Patent: Mar. 30, 2021

(54) APPARATUS AND METHOD FOR MEASURING BIOELECTRICAL IMPEDANCE AND APPARATUS AND METHOD FOR MEASURING BIOMETRIC INFORMATION

(71) Applicant: SAMSUNG ELECTRONICS CO., LTD., Suwon-si (KR)

(72) Inventors: Myoung Hoon Jung, Bucheon-si (KR); Kak Namkoong, Seoul (KR); Yeol Ho Lee, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 514 days.

(21) Appl. No.: 15/878,881

(22) Filed: Jan. 24, 2018

(65) Prior Publication Data
US 2018/0206761 A1    Jul. 26, 2018

(30) Foreign Application Priority Data
Jan. 24, 2017   (KR) .................. 10-2017-0011232

(51) Int. Cl.
*A61B 5/00*  (2006.01)
*A61B 5/0537*  (2021.01)

(52) U.S. Cl.
CPC .......... *A61B 5/0537* (2013.01); *A61B 5/4872* (2013.01); *A61B 5/4875* (2013.01); *A61B 5/7278* (2013.01)

(58) Field of Classification Search
CPC .......... A61B 5/686; A61B 2018/00875; A61B 18/1206; A61B 5/14532; A61B 5/0536; A61B 5/14546
(Continued)

(56) References Cited

U.S. PATENT DOCUMENTS 6,625,487 B2   9/2003  Herleikson
7,457,660 B2   11/2008 Smith et al.
(Continued)

FOREIGN PATENT DOCUMENTS

EP   3011901 A1   4/2016
EP   3153099 A1   4/2017
(Continued)

OTHER PUBLICATIONS

Communication dated May 30, 2018, issued by the European Patent Office in counterpart European Patent Application No. 18153196.3.

*Primary Examiner* — May A Abouelela
(74) *Attorney, Agent, or Firm* — Sughrue Mion, PLLC

(57) ABSTRACT

An apparatus for measuring bioelectrical impedance includes a current source configured to apply a constant current to an object through a first electrode and a second electrode; a measurement mode switcher configured to switch a measurement mode from a first measurement mode to a second measurement mode in response to a measurement mode switch signal; a voltmeter configured to obtain a voltage applied to a third electrode and a fourth electrode due to the constant current applied to the object; and a processor configured to obtain first impedance based on a first voltage obtained by the voltmeter immediately before start of a measurement mode switch, obtain second impedance based on a second voltage obtained by the voltmeter immediately after completion of the measurement mode switch, and obtain bioelectrical impedance of the object based on the first impedance and the second impedance.

25 Claims, 14 Drawing Sheets

(58) Field of Classification Search
USPC .................................. 600/300, 547; 702/65
See application file for complete search history.

(56) References Cited

U.S. PATENT DOCUMENTS

| | | | |
|---|---|---|---|
| 7,813,794 B2 | 10/2010 | Oku et al. | |
| 8,831,898 B2 | 9/2014 | Pinter et al. | |
| 9,078,586 B2 | 7/2015 | Fukuda et al. | |
| 9,084,583 B2 | 7/2015 | Mazar et al. | |
| 2004/0054298 A1 | 3/2004 | Masuo et al. | |
| 2006/0094979 A1 | 5/2006 | Masuo et al. | |
| 2011/0046505 A1* | 2/2011 | Cornish | A61B 5/053 600/547 |
| 2011/0208458 A1* | 8/2011 | Pinter | A61B 5/053 702/65 |
| 2015/0150478 A1* | 6/2015 | Ochi | A61B 5/0537 600/547 |
| 2015/0157240 A1* | 6/2015 | Shoudy | A61B 5/0536 600/547 |
| 2015/0201861 A1* | 7/2015 | Ko | A61B 5/0531 600/547 |
| 2015/0216441 A1* | 8/2015 | Khalfallah | A61B 5/0531 600/547 |
| 2015/0342497 A1* | 12/2015 | Maktura | A61B 5/7275 600/547 |
| 2015/0359452 A1* | 12/2015 | Giovangrandi | A61B 5/1102 600/547 |
| 2016/0106337 A1 | 4/2016 | Jung et al. | |
| 2016/0220143 A1 | 8/2016 | Jung et al. | |
| 2017/0100052 A1 | 4/2017 | Jung et al. | |

FOREIGN PATENT DOCUMENTS

| | | |
|---|---|---|
| JP | 2006271745 A | 10/2006 |
| JP | 4101654 B2 | 6/2008 |
| JP | 201124831 A | 2/2011 |
| KR | 100885396 B1 | 2/2009 |
| KR | 1020160046616 A | 4/2016 |
| WO | 2010/044026 A1 | 4/2010 |

* cited by examiner

FIG. 13B

| Subject | Z4P range [Ω] | Zm range [Ω] | | | BF range [%] | | |
|---|---|---|---|---|---|---|---|
| | | 5s | 6s | 7s | 5s | 6s | 7s |
| 1 | 102.4 | 72.3 | 70.4 | 69.1 | 1.1 | 1.1 | 1.0 |
| 2 | 39.2 | 40.2 | 40.2 | 40.3 | 0.7 | 0.7 | 0.7 |
| 3 | 35.0 | 14.6 | 15.0 | 16.1 | 0.3 | 0.3 | 0.3 |
| 4 | 199.9 | 43.3 | 38.3 | 35.1 | 1.1 | 1.0 | 0.9 |
| 5 | 194.7 | 92.2 | 94.6 | 97.3 | 1.2 | 1.2 | 1.3 |
| 6 | 145.7 | 33.2 | 35.8 | 37.9 | 0.5 | 0.6 | 0.6 |
| 7 | 220.5 | 158.4 | 159.8 | 160.9 | 2.7 | 2.7 | 2.7 |
| 8 | 107.2 | 30.0 | 30.7 | 31.1 | 0.6 | 0.6 | 0.6 |
| 9 | 13.6 | 26.2 | 26.1 | 25.7 | 0.4 | 0.4 | 0.4 |
| 10 | 18.5 | 22.9 | 23.2 | 23.1 | 0.4 | 0.4 | 0.4 |
| 11 | 45.1 | 34.7 | 35.2 | 35.2 | 0.6 | 0.6 | 0.6 |
| 12 | 40.9 | 35.3 | 35.3 | 35.0 | 0.8 | 0.8 | 0.8 |
| 13 | 39.6 | 28.7 | 29.1 | 29.2 | 0.5 | 0.5 | 0.5 |
| 14 | 84.1 | 56.4 | 57.1 | 58.0 | 1.0 | 1.0 | 1.1 |
| 15 | 45.9 | 21.4 | 21.3 | 21.3 | 0.4 | 0.4 | 0.4 |
| 16 | 19.8 | 25.1 | 25.0 | 24.8 | 0.4 | 0.4 | 0.4 |
| 17 | 39.5 | 52.9 | 52.9 | 52.3 | 0.5 | 0.5 | 0.5 |
| 18 | 59.2 | 36.4 | 35.8 | 34.9 | 0.3 | 0.3 | 0.3 |
| 19 | 34.4 | 26.7 | 26.7 | 27.1 | 0.6 | 0.6 | 0.6 |
| 20 | 86.6 | 58.1 | 58.9 | 59.9 | 1.1 | 1.1 | 1.1 |
| average | 78.600 | 45.454 | 45.575 | 45.713 | 0.754 | 0.754 | 0.754 |

APPARATUS AND METHOD FOR MEASURING BIOELECTRICAL IMPEDANCE AND APPARATUS AND METHOD FOR MEASURING BIOMETRIC INFORMATION

CROSS-REFERENCE TO RELATED APPLICATION(S)

This application claims priority from Korean Patent Application No. 10-2017-0011232, filed on Jan. 24, 2017 in the Korean Intellectual Property Office, the entire disclosure of which is incorporated herein by reference in its entirety.

BACKGROUND

1. Field

Apparatuses and methods consistent with exemplary embodiments relate to apparatuses and methods for measuring bioelectrical impedance and apparatuses and methods for measuring biometric information.

2. Description of Related Art

A variety of medical devices are being developed to diagnose patients' health conditions. The importance of medical devices for measuring electrical bio-signals of patients has been emphasized due to patient's convenience and promptness of the result of medical examination in the medical examination process.

In particular, bioelectrical impedance may be used to monitor the health or emotional state of a living body. Recently, various studies have been conducted to miniaturize devices for measuring the bioelectrical impedance and measure the bioelectrical impedance more quickly and accurately.

SUMMARY

One or more exemplary embodiments provide an apparatus and a method for measuring bioelectrical impedance more quickly and accurately.

One or more exemplary embodiments also provide an apparatus and a method for measuring bioelectrical information more quickly and accurately.

According to an aspect of an exemplary embodiment, there is provided an apparatus for measuring bioelectrical impedance, including: a first electrode; a second electrode; a third electrode; a fourth electrode; a current source configured to apply a constant current to an object through a first electrode and a second electrode; a measurement mode switcher configured to switch a measurement mode from a first measurement mode to a second measurement mode in response to a measurement mode switch signal; a voltmeter configured to obtain a voltage applied to a third electrode and a fourth electrode due to the constant current applied to the object through the first electrode and the second electrode, in the first measurement mode and the second measurement mode, respectively; and a processor configured to obtain first impedance based on a first voltage obtained by the voltmeter immediately before start of a measurement mode switch from the first measurement mode to the second measurement mode, obtain second impedance based on a second voltage obtained by the voltmeter immediately after completion of the measurement mode switch from the first measurement mode to the second measurement mode, and obtain bioelectrical impedance of the object based on the first impedance and the second impedance.

A four-point impedance measurement method may be used in the first measurement mode, and a two-point impedance measurement method may be used in the second measurement mode.

The measurement mode switcher may switch the measurement mode from the first measurement mode to the second measurement mode by short-circuiting the first electrode and the third electrode to each other and short-circuiting the second electrode and the fourth electrode to each other.

The processor may generate the measurement mode switch signal in response to determining that a predetermined period of time elapses in the first measurement mode.

The processor may generate the measurement mode switch signal in response to determining that the first impedance of the first measurement mode exceeds a predetermined first threshold.

The processor may determine a time point of the completion of the measurement mode switch from the first measurement mode to the second measurement mode.

The processor may determine the time point of the completion of the measurement mode switch from the first measurement mode to the second measurement mode by monitoring measurement impedance based on the voltage obtained by the voltmeter after the start of the measurement mode switch from the first measurement mode to the second measurement mode.

The processor may determine a time point at which a change of the measurement impedance turns from positive (+) to negative (−) as the time point of the completion of the measurement mode switch from the first measurement mode to the second measurement mode.

The apparatus may further include a controller configured to control the voltmeter, the measurement mode switcher, and the processor to repeat operations of obtaining the voltage, switching the measurement mode, and obtaining the first impedance, the second impedance, and the bioelectrical impedance until a difference between currently obtained bioelectrical impedance and bioelectrical impedance obtained immediately before the currently obtained bioelectrical impedance becomes equal to or less than a predetermined threshold.

The controller may determine the obtained bioelectrical impedance as the bioelectrical impedance of the object in response to determining that the difference between the currently obtained bioelectrical impedance and the bioelectrical impedance obtained immediately before the currently obtained bioelectrical impedance is equal to or less than the predetermined threshold.

According to an aspect of another exemplary embodiment, there is provided an apparatus for measuring bioelectrical impedance, including: a first electrode; a second electrode; a third electrode; a fourth electrode; a current source configured to apply a constant current to an object through a first electrode and a second electrode; a measurement mode switcher configured to switch a measurement mode from a second measurement mode to a first measurement mode in response to a measurement mode switch signal; a voltmeter configured to obtain a voltage applied to a third electrode and a fourth electrode due to the constant current applied to the object through the first electrode and the second electrode, in the first measurement mode and the second measurement mode, respectively; and a processor configured to obtain second impedance based on a second voltage obtained by the voltmeter immediately before start of a measurement mode switch from the second measurement mode to the first measurement mode, obtain first impedance based on a first voltage obtained by the voltmeter immediately after completion of the measurement mode switch from the second measurement mode to the first measurement mode, and obtain bioelectrical impedance of the object based on the first impedance and the second impedance.

A four-point impedance measurement method may be used in the first measurement mode, and a two-point impedance measurement method may be used in the second measurement mode.

The measurement mode switcher may switch the measurement mode from the second measurement mode to the first measurement mode by opening the first electrode and the third electrode, which are short-circuited to each other in the second measurement mode, and opening the second electrode and the fourth electrode, which are short-circuited to each other in the second measurement mode.

The processor may generate the measurement mode switch signal in response to determining that the second impedance of the second measurement mode is less than a predetermined second threshold.

The predetermined second threshold may be set in consideration of a dynamic range of the apparatus for measuring the bioelectrical impedance.

The processor may determine a time point of the completion of the measurement mode switch from the second measurement mode to the first measurement mode by monitoring measurement impedance based on the voltage obtained by the voltmeter after the start of the measurement mode switch from the second measurement mode to the first measurement mode.

The processor may determine a time point at which a change of the measurement impedance turns from negative (−) to positive (+) as the time point of the completion of the measurement mode switch from the second measurement mode to the first measurement mode.

According to an aspect of still another exemplary embodiment, there is provided a method of measuring bioelectrical impedance, including: obtaining first impedance based on a first voltage of an object obtained immediately before start of a measurement mode switch from a first measurement mode to a second measurement mode; switching a measurement mode from the first measurement mode to the second measurement mode; obtaining second impedance based on a second voltage of the object obtained immediately after completion of the measurement mode switch from the first measurement mode to the second measurement mode; and obtaining bioelectrical impedance of the object based on the first impedance and the second impedance.

A four-point impedance measurement method based on a first electrode, a second electrode, a third electrode, and a fourth electrode may be used in the first measurement mode, and a two-point impedance measurement method based on the third electrode and the fourth electrode may be used in the second measurement mode.

The switching may include switching the measurement mode from the first measurement mode to the second measurement mode by short-circuiting the first electrode and the third electrode to each other and short-circuiting the second electrode and the fourth electrode to each other.

The switching may include switching the measurement mode from the first measurement mode to the second measurement mode in response to determining that a predetermined period of time elapses in the first measurement mode and/or that the first impedance of the first measurement mode exceeds a predetermined first threshold.

The obtaining the second impedance may include determining a time point of the completion the measurement mode switch from the first measurement mode to the second measurement mode by monitoring measurement impedance based on a voltage obtained after the start of the measurement mode switch from the first measurement mode to the second measurement mode.

The determining the time point of the completion of the measurement mode switch may include determining a time point at which a change of the measurement impedance turns from positive (+) to negative (−) as the time point of the completion of the measurement mode switch from the first measurement mode to the second measurement mode.

The method may further include repeatedly performing operations of obtaining the first impedance, switching from the first measurement mode to the second measurement mode, obtaining the second impedance, and obtaining the bioelectrical impedance until a difference between currently obtained bioelectrical impedance and bioelectrical impedance obtained immediately before the currently obtained bioelectrical impedance becomes equal to or less than a predetermined threshold.

According to an aspect of still another exemplary embodiment, there is provided an apparatus for measuring biometric information, including: a first electrode; a second electrode; a third electrode; a fourth electrode; a bioelectrical impedance measurer configured to obtain bioelectrical impedance of an object; and a biometric information estimator configured to estimate biometric information of the object based on the obtained bioelectrical impedance of the object, wherein the bioelectrical impedance measurer includes: a current source configured to apply a constant current to the object through a first electrode and a second electrode; a measurement mode switcher configured to switch a measurement mode from a first measurement mode to a second measurement mode in response to a measurement mode switch signal; a voltmeter configured to obtain a voltage applied to a third electrode and a fourth electrode due to the constant current applied to the object through the first electrode and the second electrode, in the first measurement mode and the second measurement mode, respectively; and a processor configured to obtain first impedance based on a first voltage obtained by the voltmeter immediately before start of a measurement mode switch from the first measurement mode to the second measurement mode, obtain second impedance based on a second voltage measured immediately after completion of the measurement mode switch from the first measurement mode to the second measurement mode, and obtain the bioelectrical impedance of the object based on the first impedance and the second impedance.

The biometric information may include at least one of a body fat percentage, a body fat mass, a muscle mass, a skeletal muscle mass, a basal metabolic rate, an intracellular water content, an extracellular water content, a body water content, an inorganic mass, and a visceral fat content.

The biometric information estimator may estimate the biometric information by using a formula which defines a relationship between the bioelectrical impedance of the object and the biometric information of the object.

BRIEF DESCRIPTION OF THE DRAWINGS

The above and/or other aspects will be more apparent by describing certain exemplary embodiments with reference to the accompanying drawings, in which:

FIG. 13B shows comparative data between measurement accuracy in a related art bioelectric impedance measurement method and a measurement accuracy in a bioelectric impedance measurement method according to an exemplary embodiment.

DETAILED DESCRIPTION

Figure 1:
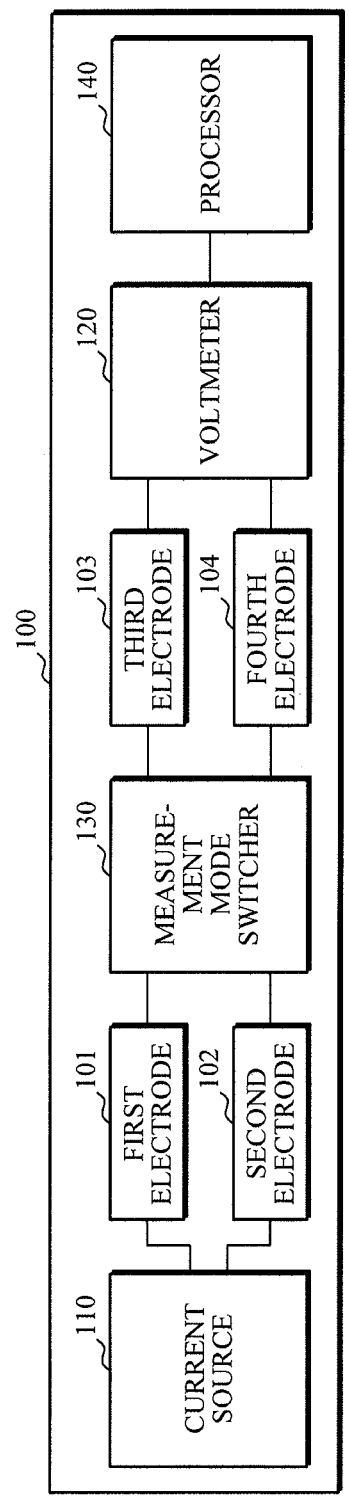
FIG. 1 is a block diagram illustrating an apparatus for measuring bioelectrical impedance according to an exemplary embodiment.

Hereinafter, various exemplary embodiments will be described in detail with reference to the accompanying drawings. Various changes, modifications, and equivalents of the systems, apparatuses and/or methods described herein are encompassed in the disclosure. In the following description, a detailed description of known functions and configurations incorporated herein will be omitted when it may obscure the subject matter with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described herein are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating an exemplary embodiment of an apparatus for measuring bioelectrical impedance.

An apparatus 100 for measuring bioelectrical impedance may be mounted in an electronic device. The electronic device may include, for example but not limited to, a mobile phone, a smartphone, a tablet computer, a notebook computer, a personal digital assistant (PDA), a portable multimedia player (PMP), a navigation system, an MP3 player, a digital camera, and a wearable device. The wearable device may include various types, such as a wristwatch type, a wrist band type, a ring type, a belt type, a necklace type, an ankle band type, a thigh band type, a forearm band type, and the like. However, the electronic device and the wearable device are not limited to the aforementioned examples.

The apparatus 100 for measuring bioelectrical impedance is an apparatus capable of measuring bioelectrical impedance of an object using bioelectrical impedance analysis (BIA) and supports a first measurement mode and a second measurement mode. In the first measurement mode, a four-point measurement method is used, which measures impedance using four electrodes, and in the second measurement mode, a two-point measurement method is used, which measures impedance using two electrodes. The apparatus 100 may obtain bioelectrical impedance based on impedances measured in the first measurement mode and the second measurement mode.

Referring to FIG. 1, the apparatus 100 includes four electrodes 101, 102, 103, and 104, a current source 110, a voltmeter 120, a measurement mode switcher 130, and a processor 140.

A first electrode 101 and a second electrode 102 are current-application electrodes used for applying a current to an object and a third electrode 103 and a fourth electrode 104 are voltage-measurement electrodes used for measuring a voltage applied to the object, due to a current applied through the first electrode 101 and the second electrode 102.

The current source 110 applies a current to the object through the first and second electrodes 101 and 102. For example, the current source 110 may apply a constant current of the same magnitude to the object through the first and second electrodes 101 and 102.

The voltmeter 120 measures a voltage of the object which is applied to both ends of the third electrode 103 and the fourth electrode 104 due to a current applied to the object through the first and second electrodes 101 and 102.

The measurement mode switcher 130 switches a measurement mode between the first measurement mode and the second measurement mode in response to a measurement mode switch signal of the processor 140. The processor 1140 may, for example, a central processor unit (CPU).

According to an exemplary embodiment, when the measurement mode switcher 130 receives a signal for switching from the first measurement mode to the second measurement mode (hereinafter, will be referred to as a "first measurement mode switch signal") from the processor 140, the measurement mode switcher 130 may switch from the first measurement mode to the second measurement mode by short-circuiting the first electrode 101 and the third electrode 103 which are open and short-circuiting the second electrode 102 and the fourth electrode 104 which are open. In addition, when the measurement mode switcher 130 receives a signal for switching from the second measurement mode to the first measurement mode (hereinafter, will be referred to as a "second measurement mode switch signal") from the processor 140, the measurement mode switcher 130 switches the measurement mode from the second measurement mode to the first measurement mode by opening the short-circuited first and third electrodes 101 and 103 and the short-circuited second and fourth electrodes 102 and 104.

The measurement mode switcher 130 may change the first measurement mode that uses four electrical electrodes into the second measurement mode that uses two electrical electrodes by short-circuiting the opened first and third electrodes 101 and 103 to each other and short-circuiting the opened second and fourth electrodes 102 and 104 to each other. In addition, the measurement mode switcher 130 may change the second measurement mode that uses two electrical electrodes into the first measurement mode that uses four electrical electrodes by opening the short-circuited first and third electrodes 101 and 103 and the short-circuited second and fourth electrodes 102 and 104. To this end, the measurement mode switcher 130 may include two switches (refer to FIG. 2). Accordingly, the voltmeter 120 measures a voltage applied to the third electrode and the fourth electrode due to the constant current applied to the object in the first measurement mode, and measures a second voltage applied to the first electrode and the second electrode due to the constant current applied to the object in the second measurement mode.

The processor 140 generates a measurement mode switch signal (e.g., the first measurement mode switch signal and the second measurement mode switch signal).

According to an exemplary embodiment, the processor 140 may generate the first measurement mode switch signal when a predetermined period of time elapses in the first measurement mode (e.g., a predetermined period of time elapses after entering the first measurement mode), and may generate the second measurement mode switch signal when a predetermined period of time elapses in the second measurement mode (e.g., a predetermined period of time elapses after entering the second measurement mode). In this case, the predetermined period of time may be set by default or according to a user's input. The predetermined period of time that is set by default may be appropriately determined based on a time to obtain sufficient measurement data in each measurement mode.

According to another exemplary embodiment, when impedance of the first measurement mode (hereinafter, will be referred to as "first impedance") which is obtained based on a voltage of the object measured in the first measurement mode (hereinafter, will be referred to as a "first voltage") is greater than a first threshold value, the processor 140 may generate the first measurement mode switch signal. When impedance of the second measurement mode (hereinafter, will be referred to as "second impedance") which is obtained based on a voltage of the object measured in the second measurement mode (hereinafter, will be referred to a "second voltage") is less than a second threshold value, the processor 140 may generate the second measurement mode switch signal. In this case, the first threshold value and the second threshold value may be set in consideration of a dynamic range of the apparatus 100.

The processor 140 may determine the completion time point of the measurement mode switch (e.g., the completion time point of measurement mode switch from the first measurement mode to the second measurement mode and/or the completion time point of measurement mode switch from the second measurement mode to the first measurement mode). In this case, the completion time point of the measurement mode switch refers to the time point when the measurement mode switch is completed in a circuit. According to an exemplary embodiment, the processor 140 may determine the completion time point of the measurement mode switch by monitoring the change in the measurement impedance obtained based on a voltage measured after the measurement mode switch starts. For example, the processor 140 may monitor the measurement impedance after the measurement mode switch starts, and determine a turning point of the sign of a differential value of the measurement impedance (e.g., in the case of the switch from the first measurement mode to the second measurement mode, the time point at which the change of the measurement impedance is turned from positive (+) to negative (−), and in the case of switch from the second measurement mode to the first measurement mode, the time point at which the change of the measurement impedance is turned from negative (−) to positive (+)) as the completion time point of the measurement mode switch.

When the first measurement mode is switched to the second measurement mode, the processor 140 obtains the first impedance immediately before the start of measurement mode switch based on the first voltage measured immediately before the start of measurement mode switch from the first measurement mode to the second measurement mode, and obtains the second impedance immediately after the completion of the measurement mode switch based on the second voltage measured immediately after the completion of measurement mode switch from the first measurement mode to the second measurement mode. In addition, when the second measurement mode is switched to the first measurement mode, the processor 140 obtains the second impedance immediately before the start of measurement mode switch based on the second voltage measured immediate before the start of measurement mode switch from the second measurement mode to the first measurement mode, and obtains the first impedance immediately after the completion of the measurement mode switch based on the first voltage measured immediately after the completion of the measurement mode switch from the second measurement mode to the first measurement mode. In this case, the time immediately before the start of the measurement mode switch may include the start time point of the measurement mode switch, and the time immediately after the completion of the measurement mode switch may include the completion time point of the measurement mode switch.

When the first measurement mode is switched to the second measurement mode, the processor 140 obtains the bioelectrical impedance of the object using a bioelectrical impedance calculation formula based on the first impedance immediately before the start of the measurement mode switch and the second impedance immediately after the completion of the measurement mode switch. In addition, when the second measurement mode is switched to the first measurement mode, the processor 140 obtains the bioelectrical impedance of the object using the bioelectric impedance formula based on the second impedance immediately before the start of the measurement mode switch and the first impedance immediately after the completion of the measurement mode switch.

Hereinafter, a process of obtaining the bioelectrical impedance calculation formula will be described with reference to FIG. 2.

Figure 2:
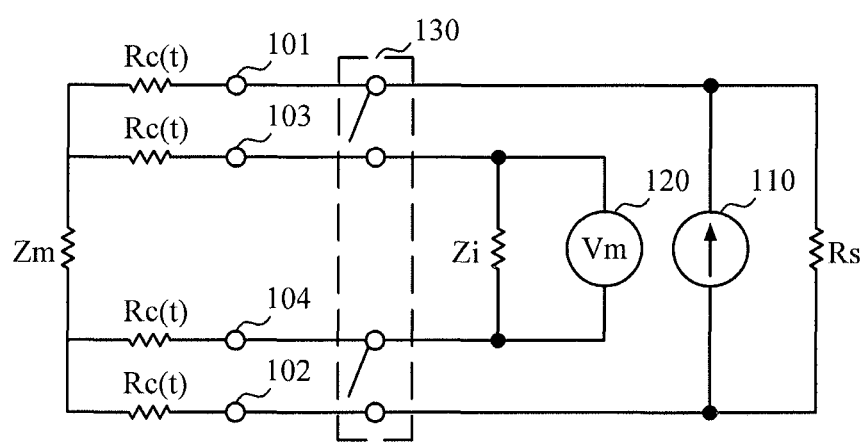
FIG. 2 is a circuit diagram for describing an apparatus for measuring bioelectrical impedance according to an exemplary embodiment.

FIG. 2 is a circuit diagram for describing an apparatus 100 for measuring bioelectrical impedance.

In FIG. 2, $Z_m$ represents bioelectrical impedance of an object, $R_c(t)$ represents contact impedance at time t, $Z_i$ represents input impedance of an analog front end (AFE), and $R_s$ represents output impedance. Here, AFE refers to an analog circuit.

Referring to FIG. 2, the first impedance $Z_{4P}(t)$ of the first measurement mode in which the first electrode 101 and the third electrode 103 are open and the second electrode 102 and the fourth electrode 104 are also open and the second impedance $Z_{2P}(t)$ of the second measurement mode in which the first electrode 101 and the third electrode 103 are short-circuited to each other and the second electrode 102 and the fourth electrode 104 are also short-circuited to each other may be each expressed in a relationship using the contact impedance $R_c(t)$, which varies with time, and the bioelectrical impedance $Z_m$ as variables.

The first impedance $Z_{4P}(t)$ and the second impedance $Z_{2P}(t)$ may be represented by Equation 1 and Equation 2, respectively.

$$Z_{4P}(t) = f_1(Z_m, R_c(t)) = \qquad (1)$$
$$Z_m \times \frac{1}{1+\frac{Z_m+2R_c(t)}{Z_i}} \times \frac{R_S}{R_s + 2R_c(t) + \frac{1}{\frac{1}{Z_m}+\frac{1}{2R_c(t)+Z_i}}}$$

$$Z_{2P}(t) = f_2(Z_m, R_c(t)) = \frac{1}{\frac{1}{Z_m+R_c(t)}+\frac{1}{Z_i}+\frac{1}{R_s}} \qquad (2)$$

As can be seen in Equation 1 and Equation 2, since contact impedance $R_c(t)$ is a value varying with time, the first impedance $Z_{4P}(t)$ and the second impedance $Z_{2P}(t)$ also vary with time. Therefore, in the related art four-point measurement method and the related art two-point measurement method, the first impedance $Z_{4P}(t)$ and the second impedance $Z_{2P}(t)$ are measured by waiting until the contact impedance $R_c(t)$ is reduced and stabilized over time so that the first impedance $Z_{4P}(t)$ and the second impedance $Z_{2P}(t)$ are stabilized. That is, time for stabilizing the first impedance $Z_{4P}(t)$ and the second impedance $Z_{2P}(t)$ is required. In addition, in the related art, the contact impedance $R_c(t)$ can be compensated using the impedance measured by the four-point measurement method and the impedance measured by the two-point measurement method. However, even in this case, a length of time for stabilizing the contact impedance $R_c(t)$ is also required in each measurement mode. Such a stabilization time may cause more time to measure the bioelectric impedance and it may be prolonged significantly depending on the user's condition or dryness of the skin. Thus, in the related art methods, it is impossible to shorten the time required for measuring bioelectrical impedance.

Referring to Equation 1 and Equation 2, the first impedance $Z_{4P}(t)$ and the second impedance $Z_{2P}(t)$ are measured values, and the input impedance $Z_i$ of the AFE and the output impedance $R_s$ of the AFE are values determined according to characteristics of the AFE. Thus, bioelectrical impedance $Z_m$ may be obtained by solving Equation 1 and Equation 2 simultaneously.

A bioelectrical impedance calculation formula derived based on Equation 1 and Equation 2 is as shown in Equation 3 (in the case of the switch from the first measurement mode to the second measurement mode) or as shown in Equation 4 (in the case of the switch from the second measurement mode to the first measurement mode).

$$Z_m = f_3(Z_{4P}(t1), Z_{2P}(t2)) \text{ where } t2 \approx t1 \text{ for } R_c(t1) = R_c(t2) \qquad (3)$$

$$Z_m = f_3(Z_{2P}(t1), Z_{4P}(t2)) \text{ where } t2 \approx t1 \text{ for } R_c(t1) = R_c(t2) \qquad (4)$$

Here, t1 is a time point immediately before the start of the measurement mode switch, and t2 is a time point immediately after the completion of the measurement mode switch. Referring to Equation 3, when t1 and t2 are very close to each other, contact impedance $R_c(t1)$ and contact impedance $R_c(t2)$ become identical to each other. Therefore, under the assumption that t1 and t2 are very close and accordingly the contact impedance $R_c(t1)$ and the contact impedance $R_c(t2)$ are identical to each other, the processor 140 may obtain the bioelectrical impedance $Z_m$ using the bioelectrical impedance calculation formula (Equation 3 or Equation 4) based on the first impedance $Z_{4P}(t1)$ or the second impedance $Z_{2P}(t1)$ immediately before the start of the measurement mode switch and the first impedance $Z_{4P}(t2)$ or the second impedance $Z_{2P}(t2)$ immediately after the completion of the measurement mode switch.

Thus, unlike the related art techniques, the apparatus 100 does not require time to stabilize the contact impedance before measuring impedance. By using the first impedance (or the second impedance) immediately before the start of the measurement mode switch and the second impedance (or the first impedance) immediately after the completion of the measurement mode switch, it is possible to estimate the changing Rc value in real time, so that an accurate bioelectrical impedance can be obtained at any measurement time. In this case, bioelectrical impedance measurement may become more accurate as the time point t1 at which the first impedance (or the second impedance) is obtained becomes closer to the time point t2 at which the second impedance (or the first impedance) is obtained. Therefore, it is possible to measure the bioelectrical impedance with a very short time.

Figure 3:
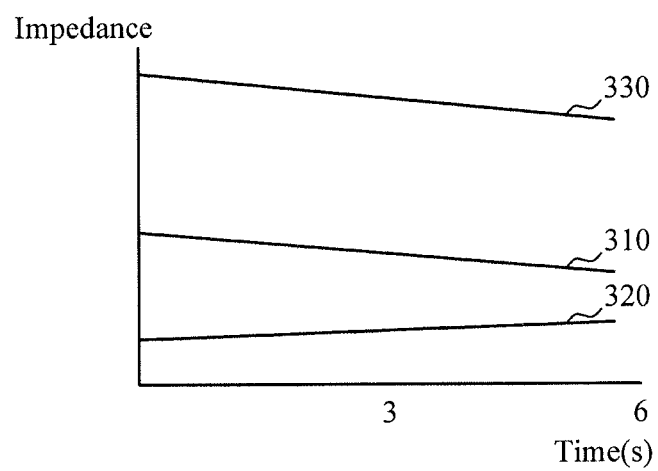
FIG. 3 is a graph for describing a relationship between contact impedance and first impedance of a first measurement mode and a relationship between the contact impedance and second impedance of a second measurement mode.

FIG. 3 is a graph for describing a relationship between the contact impedance and the first impedance of the first measurement mode and a relationship between the contact impedance and the second impedance of the second measurement mode.

Reference numeral 310 in FIG. 3 represents the contact impedance, reference numeral 320 represents the first impedance of the first measurement mode, and reference numeral 330 represents the second impedance of the second measurement mode. The contact impedance gradually decreases with time due to the perspiration of the object.

The first impedance of the first measurement mode is represented by Equation 1. The change of the first impedance due to the contact impedance may be obtained by differentiating Equation 1 with respect to the contact impedance. This is expressed by Equation 5.

$$\frac{dZ_{4P}}{dR_C} \approx \frac{-2Z_m \times Z_i // R_S}{(2R_C + Z_m + Z_i // R_S)^2} \text{ for } Z_i, R_S \gg Z_m, R_c \quad (5)$$

Figure 5:
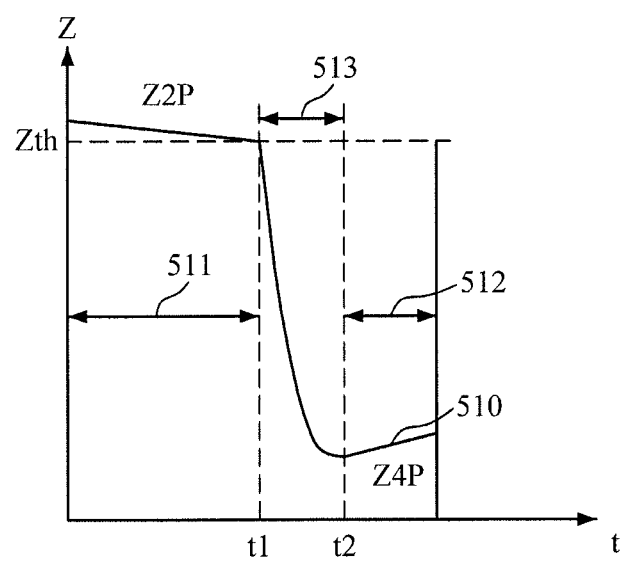
FIG. 5 is a graph for describing a bioelectrical impedance measurement method according to another exemplary embodiment.

Referring to FIG. 5, the rate of change of $Z_{4P}$ according to the change of $R_c$ during measurement in the first measurement mode is negative. Thus, as shown in FIG. 3, when $R_c$ 310 decreases, $Z_{4P}$ 320 inversely increases.

In addition, when $Z_i$ and $R_s$ are infinite, $Z_{4P}$ is constant irrespective of the change of $R_c$, but when $Z_i$ and $R_s$ are finite, $Z_{4P}$ is also changed by the change of $R_c$. In particular, as parallel impedance values of $Z_i$ and $R_s$ decrease, the rate of change of $Z_{4P}$ according to the change of $R_c$ increases more.

The second impedance of the second measurement mode is defined by Equation 2. The change of the second impedance according to the contact impedance $R_c$ may be obtained by differentiating Equation 2 with respect to the contact impedance and this is expressed by Equation 6.

$$\frac{dZ_{2P}}{dR_C} = \frac{1}{\left(1 + \frac{Z_m + R_C}{Z_i // R_S}\right)^2} \quad (6)$$

Referring to Equation 6, the rate of change of $Z_{2P}$ according to the change of $R_c$ during measurement in the second measurement mode is positive. Therefore, as shown in FIG. 3, when $R_c$ 310 decreases, $Z_{2P}$ 330 also decreases.

In addition, when $Z_i$ and $R_s$ are infinite, the rate of change of $Z_{2P}$ according to the change of Rc is 1. Thus, unless $R_c$ is saturated, $Z_{2P}$ is not saturated.

Figure 4:
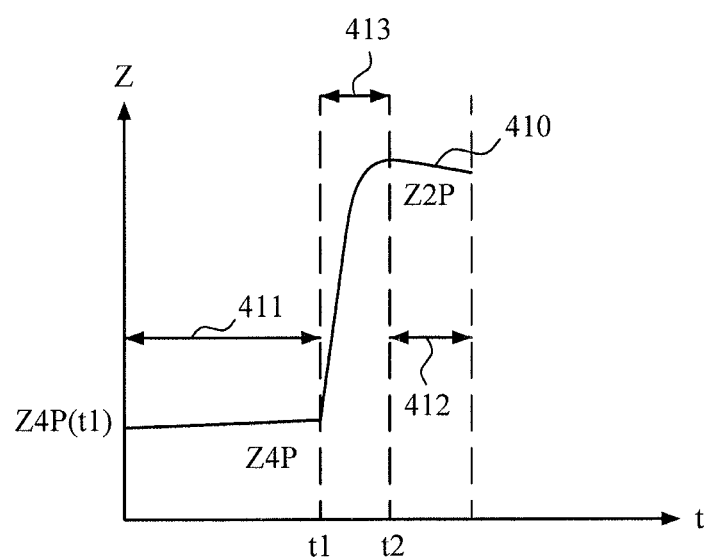
FIG. 4 is a graph for describing a bioelectrical impedance measurement method according to an exemplary embodiment.

FIG. 4 is a graph for describing an exemplary embodiment of a bioelectrical impedance measurement method.

FIG. 4 shows an example of the switch from the first measurement mode to the second measurement mode wherein, when a predetermined period of time elapses in the first measurement mode, the measurement mode is switched from the first measurement mode to the second measurement mode.

Reference numeral 410 in FIG. 4 denotes measurement impedance, reference numeral 411 denotes a first measurement mode interval, and reference numeral 412 denotes a second measurement mode interval. In addition, reference numeral 413 denotes a measurement mode switch interval.

Referring to FIGS. 1 and 4, the voltmeter 120 measures a first voltage v(t1) of the object at time point t1 after a predetermined period of time elapses in the first measurement mode, and the processor 140 obtains first impedance $Z_{4P}$(t1) based on the first voltage v(t1).

The processor 140 generates a first measurement mode switch signal at the time point t1, and the measurement mode switcher 130 switches the measurement mode from the first measurement mode to the second measurement mode by short-circuiting the first electrode 101 and the third electrode 103 to each other and short-circuiting the second electrode 102 and the fourth electrode 104 to each other.

The processor 140 monitors the measurement impedance 410 in the measurement mode switch interval 413 based on a voltage measured by the voltmeter 120 after the measurement mode switch to the second measurement mode starts, and the processor 140 determines the completion time t2 of the measurement mode switch. That is, the processor 140 monitors the measurement impedance 410 in the measurement mode switch interval 413 from the time point t1 and determines that the time point t2 at which the change of the measurement impedance 410 is turned from positive (+) to negative (−) is the completion time point of the measurement mode switch. As described with reference to FIG. 3, the contact impedance decreases with time and consequently the second impedance of the second measurement mode also decreases. Thus, it may be determined that time point t2 at which the measurement impedance 410 in the measurement mode switch interval 413 starts decreasing is the completion time point of the measurement mode switch.

The voltmeter 120 measures a second voltage v(t2) of the object at the time point t2 in the second measurement mode, and the processor 140 obtains second impedance Z2P(t2) based on the second voltage v(t2).

The processor 140 obtains the bioelectrical impedance $Z_m$ of the object using Equation 3 based on the first impedance $Z_{4P}$(t1) and the second impedance Z2P(t2).

FIG. 5 is a graph for describing another exemplary embodiment of the bioelectrical impedance measurement method.

FIG. 5 illustrates an example of switch from the second measurement mode to the first measurement mode, wherein when second measurement mode measured in the second measurement mode is less than a second threshold, the measurement mode is switched from the second measurement mode to the first measurement mode. Here, the second impedance may be set in consideration of a dynamic range of the apparatus 100 for measuring bioelectrical impedance.

Reference numeral 510 in FIG. 5 denotes measurement impedance, reference numeral 511 denotes a second measurement mode interval, and reference numeral 512 denotes a first measurement mode interval. In addition, reference numeral 513 denotes a measurement mode switch interval.

Referring to FIGS. 1 and 5, the voltmeter 120 measures a second voltage v(t) of the object in the second measurement mode, and the processor 140 monitors the measurement impedance (or second impedance Z2P(t) 510) based on the measured second voltage v(t) and determines time point t1 at which the measurement impedance (or second impedance Z2P(t) 510) becomes less than the second threshold Zth.

The processor 140 extracts the second impedance $Z_{2P}$(t1) at the time point t1 and generates a second measurement mode switch signal at the time point t1. The measurement mode switcher 130 switches the measurement mode from the second measurement mode to the first measurement mode in response to the second measurement mode switch signal by opening the short-circuited first and third electrodes 101 and 103 and opening the short-circuited second and fourth electrodes 102 and 104.

The processor 140 monitors the measurement impedance 510 in the measurement mode switch interval 510 based on a voltage measured by the voltmeter 120 after the measurement mode switch to the first measurement mode starts, and the processor 140 determines the completion time t2 of the measurement mode switch. That is, the processor 140 monitors the measurement impedance 510 from the start time of the measurement mode switch, (e.g., the time point t1), and determines that the time point t2 at which the change of the measurement impedance 510 is turned from negative (−) to positive (+) is the completion time point of the measurement mode switch. As described with reference to FIG. 3, the contact impedance decreases with time and accordingly, the first impedance of the first measurement mode increases. Therefore, the time point t2 at which the measurement impedance 510 in the measurement mode switch interval 513 starts increasing may be determined to be the completion time point of the measurement mode switch.

The voltmeter 120 measures the first voltage v(t1) at the time point t2 in the first measurement mode, and the processor 140 obtains the first impedance Z4P(t2) based on the first voltage v(t2).

The processor 140 obtains the bioelectrical impedance $Z_m$ of the object using Equation 4 based on the second impedance $Z_{2P}$(t1) and the first impedance Z4P(t2).

Figure 6:
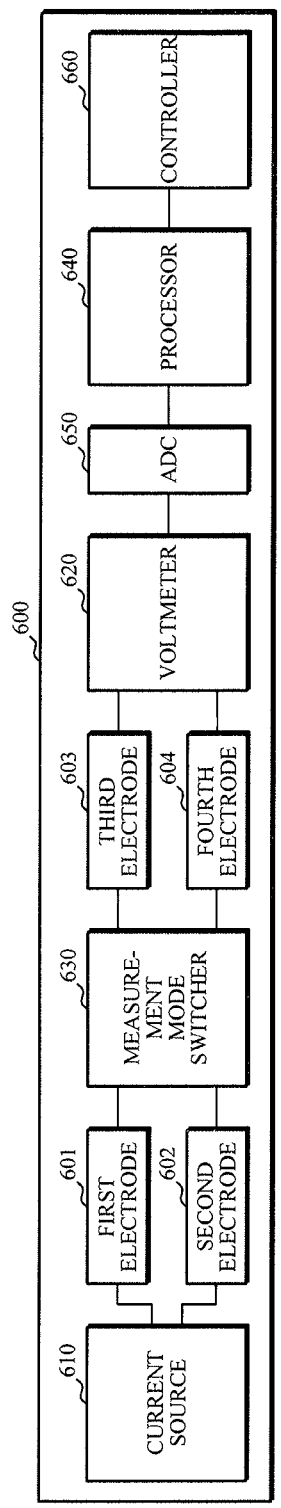
FIG. 6 is a block diagram illustrating an apparatus for measuring bioelectrical impedance according to another exemplary embodiment.

FIG. 6 is a block diagram illustrating another exemplary embodiment of the apparatus for measuring bioelectrical impedance.

Referring to FIG. 6, an apparatus 600 for measuring bioelectrical impedance includes four electrodes, 601, 602, 603, and 604, a current source 610, a voltmeter 620, a measurement mode switcher 630, a processor 640, an analog-to-digital converter (ADC) 650, and a controller 660. Here, the four electrodes 601 to 604, the current source 610, the voltmeter 620, the measurement mode switcher 630, and the processor 640 are the same as the four electrodes 101 to 104, the current source 110, the voltmeter 120, the measurement mode switcher 130, and the processor 140 of FIG. 1, and thus detailed descriptions thereof will not be reiterated.

The ADC 650 may convert a voltage, which is input as an analog signal, into a digital signal.

The controller 660 may repeatedly perform calculation of bioelectrical impedance by controlling the current source 610, the voltmeter 620, the measurement mode switcher 630, and the processor 640. For example, the controller 650 may control the current source 610, the voltmeter 620, the measurement mode switcher 630, and the processor 640 such that measurement of a first voltage, calculation of first impedance, measurement mode switch, measurement of a second voltage, calculation of second impedance, and calculation of bioelectrical impedance are repeatedly performed until a difference between the most recently obtained bioelectrical impedance and bioelectrical impedance obtained immediately before said bioelectrical impedance becomes equal to or less than a predetermined threshold. In addition, when the difference between the most recently obtained bioelectrical impedance and the bioelectrical impedance obtained immediately before said bioelectrical impedance is equal to or less than the predetermined threshold, the controller 650 may stop repeating the process and determine the last obtained bioelectrical impedance as the bioelectrical impedance of the object.

Figure 7:
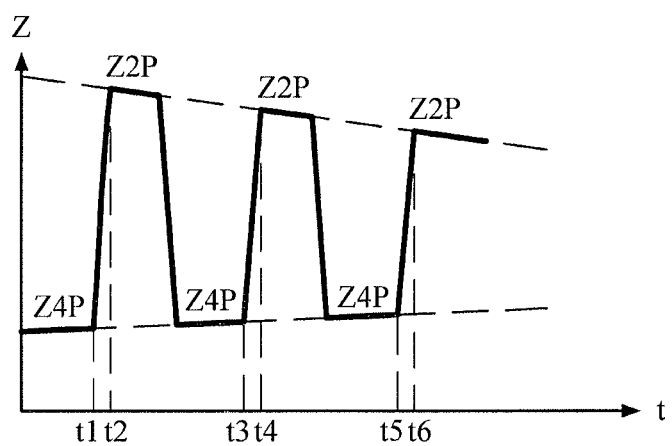
FIG. 7 is a graph for describing a bioelectrical impedance measurement method according to another exemplary embodiment.

FIG. 7 is a graph for describing another exemplary embodiment of the bioelectrical impedance measurement method.

FIG. 7 shows an example in which measurement mode switch is performed when a predetermined period of time elapses in each measurement mode. The change of measurement impedance in a measurement mode switch interval is shown as a straight line in FIG. 7 for convenience of illustration.

Referring to FIGS. 6 and 7, the voltmeter 620 measures a first voltage v(t1) of the object at time point t1 after a predetermined period of time elapses in the first measurement mode, and the processor 640 obtains first impedance $Z_{4P}$(t1) based on the first voltage v(t1).

The processor 640 generates a first measurement mode switch signal at the time point t1, and the measurement mode switcher 630 switches the measurement mode from the first measurement mode to the second measurement mode by short-circuiting the first electrode 601 and the third electrode 603 to each other and short-circuiting the second electrode 602 and the fourth electrode 604 to each other.

The processor 640 monitors measurement impedance in the measurement mode switch interval based on a voltage measured by the voltmeter 620 after the start of the measurement mode switch to the second measurement mode and determines the completion time t2 of the measurement mode switch. That is, the processor 640 monitors the measurement impedance in the measurement mode switch interval from the time point t1 and determines that the time point t2 at which the change of the measurement impedance is turned from positive (+) to negative (−) is the completion time point of the measurement mode switch.

The voltmeter 620 measures a second voltage v(t2) of the object at the time point t2 in the second measurement mode, and the processor 640 obtains second impedance Z2P(t2) based on the second voltage v(t2).

The processor 640 obtains the bioelectrical impedance $Z_{m1}$ of the object using Equation 3 based on the first impedance $Z_{4P}$(t1) and the second impedance $Z_{2P}$(t2).

The processor 640 generates a second measurement mode switch signal at a time point after a predetermined period of time elapses in the second measurement mode, under the control of the controller 660, and the measurement mode switcher 630 switches the measurement mode from the second measurement mode to the first measurement mode by opening the short-circuited first and third electrodes 601 and 603 and the short-circuited second and fourth electrodes 602 and 604 in response to the second measurement mode switch signal.

The voltmeter 620 measures a first voltage v(t3) of the object at time point t3 after a predetermined period of time elapses in the first measurement mode, and the processor 640 obtains first impedance $Z_{4P}$(t3) based on the first voltage v(t3).

The processor 640 generates the first measurement mode switch signal at the time point t3, and the measurement mode switcher 630 switches the measurement mode from the first measurement mode to the second measurement mode by short-circuiting the first and third electrodes 601 and 603 to each other and short-circuiting the second and fourth electrodes 602 and 604 to each other in response to the first measurement mode switch signal.

The processor 640 monitors measurement impedance in the measurement mode switch interval based on a voltage measured by the voltmeter 620 after the start of the measurement mode switch to the second measurement mode and determines the completion time t4 of the measurement mode switch. That is, the processor 640 monitors the measurement impedance in the measurement mode switch interval from the time point t3 and determines that the time point t4 at which the change of the measurement impedance is turned from positive (+) to negative (−) is the completion time point of the measurement mode switch.

The voltmeter 640 measures a second voltage v(t4) of the object at the time point t4 in the second measurement mode, and the processor 640 obtains second impedance $Z_{2P}$(t4) based on the second voltage v(t4).

The processor 640 obtains the bioelectrical impedance $Z_{m2}$ of the object using Equation 3 based on the first impedance $Z_{2P}$(t3) and the second impedance $Z_{2P}$(t4).

The controller 660 determines whether a difference between the bioelectrical impedance $Z_{m2}$ and the bioelectrical impedance $Z_{m1}$ is equal to or less than a predetermined threshold.

When the difference between the bioelectrical impedance $Z_{m2}$ and the bioelectrical impedance $Z_{m1}$ is not equal to or less than the predetermined threshold, the processor 640 generates the second measurement mode switch signal at a time point after a predetermined period of time elapses in the second measurement mode, under the control of the controller 660, and the measurement mode switcher 630 switches the measurement mode from the second measurement mode to the first measurement mode by opening the short-circuited first and third electrodes 601 and 603 and the short-circuited second and fourth electrodes 602 and 604 in response to the second measurement mode switch signal.

The voltmeter 620 measures a first voltage v(t5) of the object at time point t5 after a predetermined period of time elapses in the first measurement mode, and the processor 640 obtains first impedance $Z_{4P}$(t5) based on the first voltage v(t5).

The processor 640 generates a first measurement mode switch signal at the time point t5, and the measurement mode switcher 630 switches the measurement mode from the first measurement mode to the second measurement mode by short-circuiting the first and third electrodes 601 and 603 to each other and the second and fourth electrodes 602 and 604 to each other in response to the first measurement mode switch signal.

The processor 640 monitors measurement impedance in the measurement mode switch interval based on a voltage measured by the voltmeter 620 after the start of the measurement mode switch to the second measurement mode and determines the completion time t6 of the measurement mode switch. That is, the processor 640 monitors the measurement impedance in the measurement mode switch interval from the time point t5 and determines that the time point t6 at which the change of the measurement impedance is turned from positive (+) to negative (−) is the completion time point of the measurement mode switch.

The voltmeter 640 measures a second voltage v(t6) of the object at the time point t6 in the second measurement mode, and the processor 640 obtains second impedance $Z_{2P}$(t6) based on the second voltage v(t6).

The processor 640 obtains the bioelectrical impedance $Z_{m3}$ of the object using Equation 3 based on the first impedance $Z_{4P}$(t5) and the second impedance $Z_{2P}$(t6).

The controller 660 determines whether a difference between the bioelectrical impedance $Z_{m3}$ and the bioelectrical impedance $Z_{m2}$ is equal to or less than a predetermined threshold. When the difference between the bioelectrical impedance $Z_{m3}$ and the bioelectrical impedance $Z_{m2}$ is equal to or less than the predetermined threshold, the controller 660 determines the bioelectrical impedance $Z_{m3}$ as the bioelectrical impedance of the object.

Figure 8:
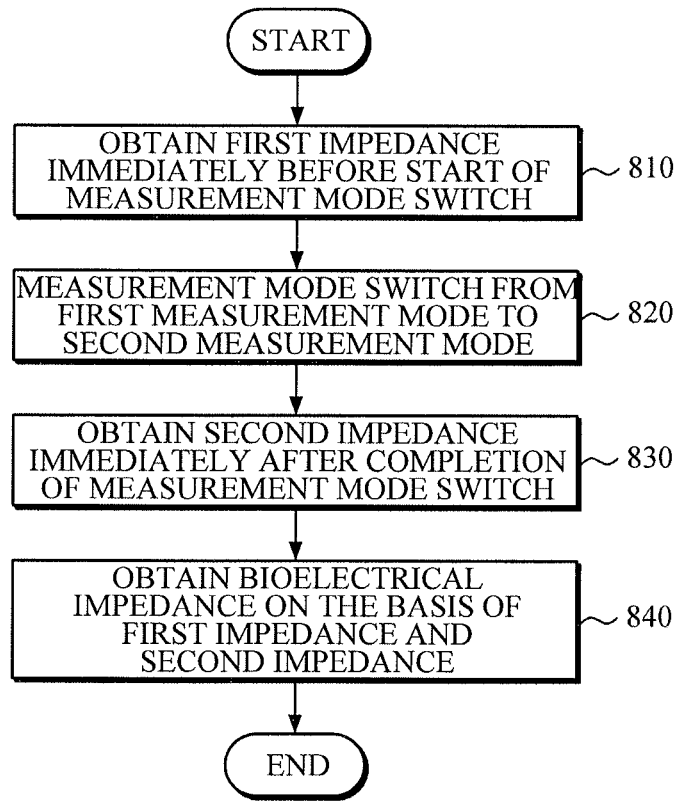
FIG. 8 is a flowchart illustrating a method of measuring bioelectrical impedance according to an exemplary embodiment.

FIG. 8 is a flowchart illustrating an exemplary embodiment of a method of measuring bioelectrical impedance.

The method of measuring bioelectrical impedance of FIG. 8 may be performed by the apparatus 100 for measuring bioelectrical impedance of FIG. 1.

Referring to FIGS. 1 and 8, the apparatus 100 for measuring bioelectrical impedance obtains first impedance immediately before the start of measurement mode switch from the first measurement mode to the second measurement mode (operation 810). For example, the apparatus 100 may measure a first voltage of an object immediately before the start of measurement mode switch from the first measurement mode to the second measurement mode, wherein the first voltage of the object is applied to both ends of the third electrode 103 and the fourth electrode 104 due to a current applied to the object through the first and second electrodes 101 and 102. Then, the apparatus 100 may obtain first impedance based on the first voltage measured immediately before the start of the measurement mode switch.

The apparatus 100 switches the measurement mode from the first measurement mode to the second measurement mode (operation 820). For example, the apparatus 100 may generate a first measurement mode switch signal by short-circuiting the first electrode 101 and the third electrode 103 to each other and short-circuiting the second electrode 102 and the fourth electrode 104 to each other when at least one of a condition that a predetermined period of time elapses in the first measurement mode and a condition that the first impedance exceeds a first threshold is satisfied.

The apparatus 100 obtains second impedance immediately after the completion of the measurement mode switch from the first measurement mode to the second measurement mode (operation 830). For example, the apparatus 100 may determine the completion time point of the measurement mode switch from the first measurement mode to the second measurement mode, and measure a second voltage of the object immediately after the completion of the measurement mode switch, wherein the second voltage is applied to the third electrode 103 short-circuited to the first electrode 101 and the fourth electrode 104 short-circuited to the second electrode 102 due to the current applied to the object through the first electrode 101 short-circuited to the third electrode 103 and the second electrode 102 short-circuited to the fourth electrode 104. Then, the apparatus 100 may obtain the second impedance immediately after the completion of the measurement mode switch based on the second voltage measured immediately after the completion of the measurement mode switch.

In this case, the apparatus 100 may determine the completion time point of the measurement mode switch by monitoring the change of measurement impedance based on a voltage measured after the measurement mode switch starts. For example, the apparatus 100 may monitor the measurement impedance after the measurement mode switch starts, and determine a turning point of the sign of a differential value of the measurement impedance (e.g., the time point at which the change of the measurement impedance is turned from positive (+) to negative (−)) as the completion time point of the measurement mode switch.

The apparatus 100 obtains bioelectrical impedance of the object based on the first impedance immediately before the start of the measurement mode switch from the first measurement mode to the second measurement mode and the second impedance immediately after the completion of the measurement mode switch from the first measurement mode to the second measurement mode (operation 840). For example, the apparatus 100 may obtain the bioelectrical impedance of the object using Equation 3 based on the first impedance immediately before the start of the measurement mode switch and the second impedance immediately after the completion of the measurement mode switch.

Figure 9:
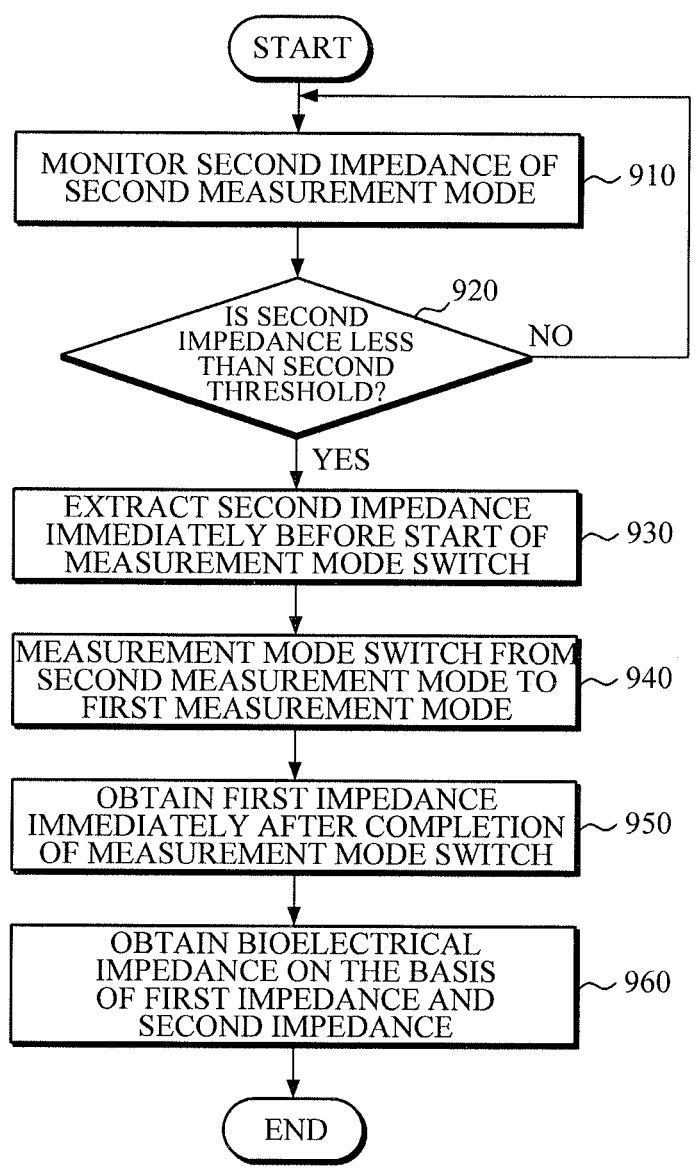
FIG. 9 is a flowchart illustrating a method of measuring bioelectrical impedance according to another exemplary embodiment.

FIG. 9 is a flowchart illustrating another exemplary embodiment of the method of measuring bioelectrical impedance.

The method of measuring bioelectrical impedance of FIG. 9 may be performed by the apparatus for measuring bioelectrical impedance of FIG. 1.

Referring to FIGS. 1 and 9, the apparatus 100 monitors second impedance of the second measurement mode (operation 910). For example, the apparatus 100 may measure a first voltage of the object which is applied to the third electrode 103 short-circuited to the first electrode 101 and the fourth electrode 104 short-circuited to the second electrode 102 due to a current applied to the object through the first electrode 101 short-circuited to the third electrode 103 and the second electrode 102 short-circuited to the fourth electrode 104, and may monitor the second impedance of the second measurement mode based on the measured first voltage.

The apparatus 100 determines whether the second impedance is less than a second threshold (operation 920). When the second impedance is equal to or greater than the second threshold, the apparatus 100 returns to operation 910 and monitors the second impedance of the second measurement mode.

When the second impedance is less than the second threshold, the apparatus 100 extracts the second impedance and determines that the extracted second impedance as second impedance immediately before start of the measurement mode switch (operation 930).

The apparatus 100 switches the measurement mode from the second measurement mode to the first measurement mode (operation 940). For example, the apparatus 100 may switch the measurement mode from the second measurement mode to the first measurement mode by opening the short-circuited first and third electrodes 101 and 103 and opening the short-circuited second and fourth electrodes 102 and 104.

The apparatus 100 obtains first impedance immediately after the completion of the measurement mode switch from the second measurement mode to the first measurement mode (operation 950). For example, the apparatus 100 may determine the completion time point of the measurement mode switch from the second measurement mode to the first measurement mode, and measure a first voltage of the object immediately after the measurement mode switch completes, wherein the first voltage is applied to the third electrode 103 and the fourth electrode 104 due to a current applied to the object through the first electrode 101 and the second electrode 102. Then, the apparatus 100 may obtain the first impedance based on the first voltage measured immediately after the measurement mode switch completes.

In this case, the apparatus 100 may determine the completion time point of the measurement mode switch by monitoring the change of measurement impedance based on a voltage measured after the measurement mode switch starts. For example, the apparatus 100 may monitor the measurement impedance after the measurement mode switch starts, and determine a turning point of the sign of a differential value of the measurement impedance (e.g., the time point at which the change of the measurement impedance is turned from negative (−) to positive (+)) as the completion time point of the measurement mode switch.

The apparatus 100 obtains bioelectrical impedance of the object based on the second impedance immediately before the start of the measurement mode switch from the second measurement mode to the first measurement mode and the first impedance immediately after the completion of the measurement mode switch from the second measurement mode to the first measurement mode (operation 960). For example, the apparatus 100 may obtain the bioelectrical impedance of the object using Equation 4 based on the second impedance immediately before the start of the measurement mode switch and the first impedance immediately after the completion of the measurement mode switch.

Figure 10:
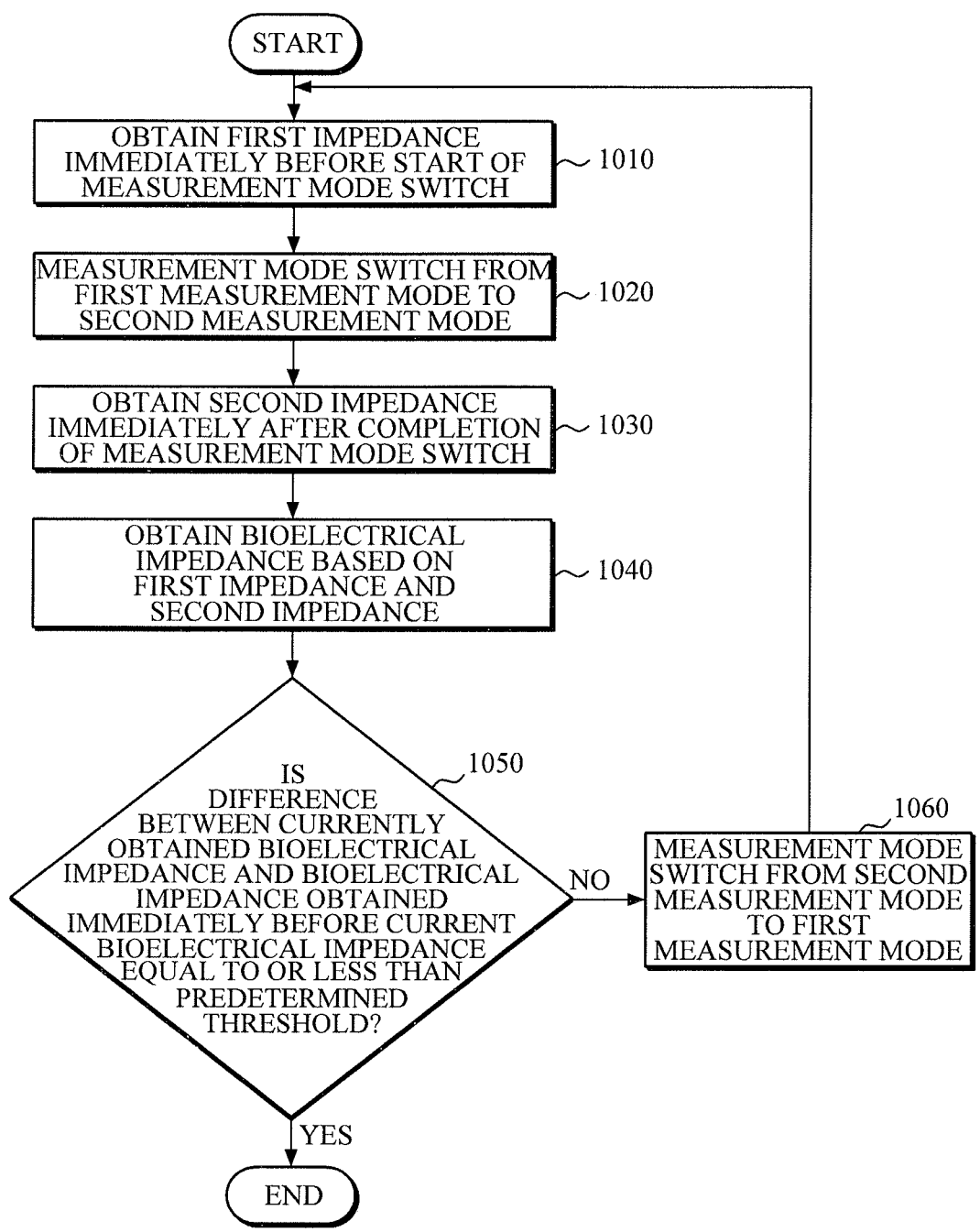
FIG. 10 is a flowchart illustrating a method of measuring bioelectrical impedance according to an exemplary embodiment.

FIG. 10 is a flowchart illustrating an exemplary embodiment of a method of measuring bioelectrical impedance.

The method of measuring bioelectrical impedance of FIG. 10 may be performed by the apparatus 600 for measuring bioelectrical impedance of FIG. 6.

Referring to FIGS. 6 and 10, the apparatus 600 obtains first impedance immediately before the start of measurement mode switch from the first measurement mode to the second measurement mode (operation 1010). For example, the apparatus 600 may measure a first voltage of the object immediately before the start of measurement mode switch from the first measurement mode to the second measurement mode, wherein the first voltage of the object is applied to the third electrode 103 and the fourth electrode 104 due to a current applied to the object through the first electrode 101 and the second electrode 102. Then, the apparatus 600 may obtain the first impedance immediately before the start of the measurement mode switch based on the first voltage measured immediately before the start of the measurement mode switch.

The apparatus 600 switches the measurement mode from the first measurement mode to the second measurement mode (operation 1020). For example, the apparatus 600 may switch the measurement mode from the first measurement mode to the second measurement mode by short-circuiting the first electrode 101 and the third electrode 103 to each other and short-circuiting the second electrode 102 and the fourth electrode 104 to each other when at least one of a condition that a predetermined period of time elapses in the first measurement mode and a condition that the first impedance exceeds a first threshold is satisfied.

The apparatus 600 obtains second impedance immediately after the completion of the measurement mode switch from the first measurement mode to the second measurement mode (operation 1030). For example, the apparatus 600 may determine the completion time point of the measurement mode switch from the first measurement mode to the second measurement mode and measure a second voltage of the object which is applied to the third electrode 103 short-circuited to the first electrode 101 and the fourth electrode 104 short-circuited to the second electrode 102 due to a current applied to the object through the first electrode 101 short-circuited to the third electrode 103 and the second electrode 102 short-circuited to the fourth electrode 104. Then, the apparatus 600 may obtain the second impedance immediately after completion of the measurement mode switch, based on the second voltage of the object measured immediately after the completion of the measurement mode switch.

In this case, the apparatus 600 may determine the completion time point of the measurement mode switch by monitoring the change of measurement impedance based on a voltage measured after the measurement mode switch starts. For example, the apparatus 600 may monitor the measurement impedance after the measurement mode switch starts, and determine a turning point of the sign of a differential value of the measurement impedance (e.g., the time point at which the change of the measurement impedance is turned from positive (+) to negative (−)) as the completion time point of the measurement mode switch.

The apparatus 600 obtains bioelectrical impedance of the object based on the first impedance immediately before the start of the measurement mode switch from the first measurement mode to the second measurement mode and based on the second impedance immediately after the completion of the measurement mode switch from the first measurement mode to the second measurement mode (operation 1040).

For example, the apparatus 600 may obtain the bioelectrical impedance of the object using Equation 3 based on the first impedance immediately before the start of the measurement mode switch and based on the second impedance immediately after the completion of the measurement mode switch.

The apparatus 600 compares the most recently obtained bioelectrical impedance with bioelectrical impedance obtained immediately before the last bioelectrical impedance and determines whether a difference between the two bioelectrical impedances is equal to or less than a predetermined threshold (operation 1050).

When the difference between the most recently obtained bioelectrical impedance and the bioelectrical impedance measured immediately before said bioelectrical impedance exceeds the predetermined threshold, the apparatus 600 switches a measurement mode from the second measurement mode to the first measurement mode (operation 1060), and returns to operation 1010 to obtain the first impedance immediately before the start of the measurement mode switch from the first measurement mode to the second measurement mode. That is, the apparatus 600 repeatedly perform operations 1010 to 1060 until the difference between the most recently obtained bioelectrical impedance and the bioelectric impedance measured immediately before the last bioelectrical impedance becomes equal to or less than the predetermined threshold.

When the difference between the most recently obtained bioelectrical impedance and the bioelectric impedance measured immediately before the last bioelectrical impedance is equal to or less than the predetermined threshold, the apparatus 600 determines the most recently obtained bioelectrical impedance as the bioelectrical impedance of the object and terminates the operation.

Figure 11:
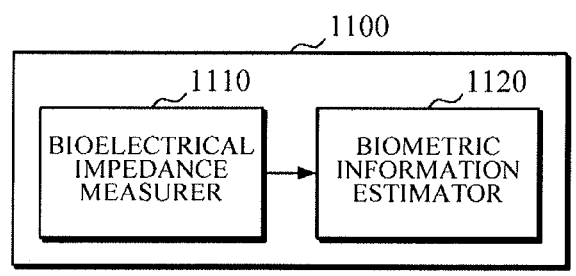
FIG. 11 is a block diagram illustrating an apparatus for measuring biometric information according to an exemplary embodiment.

FIG. 11 is a block diagram illustrating an exemplary embodiment of an apparatus for measuring biometric information.

An apparatus 1100 for measuring biometric information may be mounted on an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include various types, such as a wristwatch type, a wrist band type, a ring type, a belt type, a necklace type, an ankle band type, a thigh band type, a forearm band type, and the like. However, the electronic device and the wearable device are not limited to the aforementioned examples.

Referring to FIG. 11, the apparatus 100 for measuring biometric information includes a bioelectrical impedance measurer 1110 and a biometric information estimator 1120.

The bioelectrical impedance measurer 1110 which is a device capable of measuring bioelectrical impedance of an object is the same as the apparatuses 100 and 600 for measuring bioelectrical impedance described with reference to FIGS. 1 to 10, and hence a detailed description thereof will not be reiterated.

The biometric information estimator 1120 may estimate biometric information of the object based on the bioelectrical impedance of the object measured by the bioelectrical impedance measurer 1110. In this case, the biometric information may include body fat percentage, body fat mass, muscle mass, skeletal muscle mass, basal metabolic rate, intracellular water content, extracellular water content, body water content, inorganic mass, visceral fat content and the like.

According to an exemplary embodiment, the biometric information estimator 1120 may estimate biometric information of the object using a biometric information calculating formula. In this case, the biometric information calculating formula may define the relationship among biometric impedance, body information, and biometric information, and may be experimentally derived in advance. The body information may include sex, age, height, weight, and the like.

Figure 12:
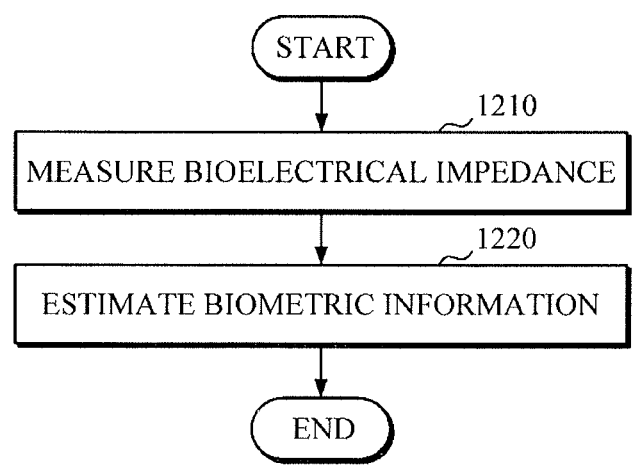
FIG. 12 is a flowchart illustrating a method of measuring biometric information according to an exemplary embodiment.

FIG. 12 is a flowchart illustrating an exemplary embodiment of a method of measuring biometric information.

The method of measuring biometric information of FIG. 12 may be performed by the apparatus 1100 for measuring biometric information of FIG. 11.

Referring to FIGS. 11 and 12, the apparatus 1100 for measuring biometric information measures bioelectrical impedance of an object (operation 1210).

The apparatus 1100 estimates biometric information of the object based on the measured bioelectrical impedance (operation 1220). In this case, the biometric information may include body fat percentage, body fat mass, muscle mass, skeletal muscle mass, basal metabolic rate, intracellular water content, extracellular water content, body water content, inorganic mass, visceral fat content and the like.

According to an exemplary embodiment, the apparatus 1100 may estimate the biometric information using a biometric information calculating formula. In this case, the biometric information calculating formula may define the relationship among biometric impedance, body information, and biometric information, and may be experimentally derived in advance. The body information may include sex, age, height, weight, and the like.

Figure 13A:
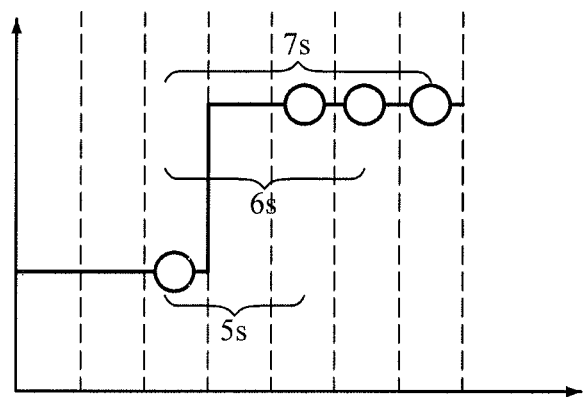
FIG. 13A is a schematic view illustrating a comparison between measurement time in a related art bioelectric impedance measurement method and measurement time in a bioelectric impedance measurement method according to an exemplary embodiment.

FIG. 13A is a schematic view illustrating a comparison between measurement time in a related art bioelectric impedance measurement method and measurement time in a bioelectric impedance measurement method according to an exemplary embodiment.

Referring to FIG. 13A, it is assumed that a measurement time of each mode is set to 3 seconds and a time interval of 1 second is set for mode switching between the first measurement mode and the second measurement mode. However, this is only an example and the disclosure is not limited thereto. For convenience of illustration, the change of measurement impedance is schematically illustrated and the measurement mode switch interval is not clearly shown in FIG. 13A.

In the example of FIG. 13A, according to the related art technique for measuring bio-impedance, a total measurement time may be a total of a measurement time (3 S) in the first measurement mode, a measurement mode switch interval (1 S), and a measurement time (3 S) in the second measurement mode (3 S). That is, the total measurement time may be seven seconds (3 S+1 S+3 S=7 S). Thus, the related art technique is disadvantageous in that the measurement time is lengthened since measurement is carried out twice by switching the measurement mode and a length of time for stabilizing the contact resistance is required in each measurement mode.

On the other hand, according to a method of measuring bio-impedance according to an exemplary embodiment, the impedance measurement time may be shortened because time for stabilizing the contact impedance before measuring impedance is not required. For example, according to an exemplary embodiment, a total measurement time may be a total of a measurement time (3 S) in the first measurement mode, a measurement mode switch interval (1 S), and a measurement time (1 S) in the second measurement mode (3

S). That is, the total measurement time may be five seconds (3 S+1 S+1 S=5 S). Thus, according to an exemplary embodiment, the bio-impedance may be measured more quickly.

FIG. 13B shows comparative data between measurement accuracy in a related art bioelectric impedance measurement method and a measurement accuracy in a bioelectric impedance measurement method according to an exemplary embodiment.

Referring to FIG. 13B, the first impedance $Z_{4P}(t)$ of the first measurement mode, the bioelectrical impedance $Z_m$, and a body fat percentage are measured for twenty subjects by using a wrist type body fat scale measuring device. As shown in FIG. 13B, the measurement using a bio-impedance measurement method according to an exemplary embodiment (e.g., corresponding to the measurement time of 5 S) and the measurement of the related art contact resistance compensation measurement method (e.g., corresponding to the measurement time of 7 S) have substantially the same measurement accuracy. Accordingly, it can be seen that when the bio-impedance measurement method according to an exemplary embodiment is used, the measurement time can be shortened (e.g., from 7 S to 5 S) while having the same measurement accuracy.

The current embodiments can be implemented as computer readable codes in a computer readable record medium. Codes and code segments constituting the computer program can be easily inferred by a skilled person in the art. The computer readable record medium includes all types of record media in which computer readable data are stored. Examples of the computer readable record medium include a read only memory (ROM), a random access memory (RAM), a compact-disk (CD)-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units represented by a block as illustrated in the drawings may be embodied as various numbers of hardware, software and/or firmware structures that execute respective functions described above, according to an embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or be implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the embodiments may be implemented in algorithms that execute on one or more processors. Furthermore, the components, elements or units represented by a block or processing steps may employ any number of related art techniques for electronics configuration, signal processing and/or control, data processing and the like.

Although a few embodiments have been shown and described, it would be appreciated by those skilled in the art that changes may be made in exemplary embodiments without departing from the principles and spirit of the disclosure, the scope of which is defined in the claims and their equivalents.

What is claimed is:

1. An apparatus for measuring a bioelectrical impedance, the apparatus comprising:
   a first electrode;
   a second electrode;
   a third electrode;
   a fourth electrode;
   a current source configured to apply a constant current to an object through the first electrode and the second electrode;
   a measurement mode switcher comprising a first switch between the first electrode and the third electrode and a second switch between the second electrode and the fourth electrode, the measurement mode switcher being configured to switch a measurement mode from a first measurement mode to a second measurement mode by controlling the first switch and the second switch in response to a measurement mode switch signal;
   a voltmeter configured to obtain a voltage applied to the third electrode and the fourth electrode due to the constant current applied to the object through the first electrode and the second electrode, in the first measurement mode and the second measurement mode, respectively; and
   a processor configured to:
      obtain a first impedance based on a first voltage obtained by the voltmeter immediately before start of a measurement mode switch from the first measurement mode to the second measurement mode;
      determine a time point of completion of the measurement mode switch from the first measurement mode to the second measurement mode, and obtain a second impedance based on a second voltage obtained by the voltmeter immediately after the completion of the measurement mode switch from the first measurement mode to the second measurement mode; and
      obtain a bioelectrical impedance of the object based on the first impedance and the second impedance.

2. The apparatus of claim 1, wherein a four-point impedance measurement method is used in the first measurement mode, and a two-point impedance measurement method is used in the second measurement mode.

3. The apparatus of claim 1, wherein the measurement mode switcher is further configured to switch the measurement mode from the first measurement mode to the second measurement mode by short-circuiting the first electrode and the third electrode to each other by using the first switch and short-circuiting the second electrode and the fourth electrode to each other by using the second switch.

4. The apparatus of claim 1, wherein the processor is further configured to generate the measurement mode switch signal in response to determining that a predetermined period of time elapses in the first measurement mode.

5. The apparatus of claim 1, wherein the processor is further configured to generate the measurement mode switch signal in response to determining that the first impedance of the first measurement mode exceeds a predetermined first threshold.

6. The apparatus of claim 1, wherein the processor is further configured to determine the time point of the completion of the measurement mode switch from the first measurement mode to the second measurement mode by monitoring a measurement impedance based on the voltage obtained by the voltmeter after the start of the measurement mode switch from the first measurement mode to the second measurement mode.

7. The apparatus of claim 6, wherein the processor is further configured to determine a time point at which a change of the measurement impedance turns from positive (+) to negative (−) as the time point of the completion of the measurement mode switch from the first measurement mode to the second measurement mode.

8. The apparatus of claim 1, further comprising:
a controller configured to control the voltmeter, the measurement mode switcher, and the processor to repeat operations of obtaining the voltage, switching the measurement mode, and obtaining the first impedance, the second impedance, and the bioelectrical impedance until a difference between a currently obtained bioelectrical impedance and a bioelectrical impedance obtained immediately before the currently obtained bioelectrical impedance becomes equal to or less than a predetermined threshold.

9. The apparatus of claim 8, wherein the controller is further configured to determine the obtained bioelectrical impedance as the bioelectrical impedance of the object in response to determining that the difference between the currently obtained bioelectrical impedance and the bioelectrical impedance obtained immediately before the currently obtained bioelectrical impedance is equal to or less than the predetermined threshold.

10. An apparatus for measuring a bioelectrical impedance, the apparatus comprising:
a first electrode;
a second electrode;
a third electrode;
a fourth electrode;
a current source configured to apply a constant current to an object through the first electrode and the second electrode;
a measurement mode switcher comprising a first switch between the first electrode and the third electrode and a second switch between the second electrode and the fourth electrode, the measurement mode switcher being configured to switch a measurement mode from a second measurement mode to a first measurement mode by controlling the first switch and the second switch in response to a measurement mode switch signal;
a voltmeter configured to obtain a voltage applied to the third electrode and the fourth electrode due to the constant current applied to the object through the first electrode and the second electrode, in the first measurement mode and the second measurement mode, respectively; and
a processor configured to:
obtain a second impedance based on a second voltage obtained by the voltmeter immediately before start of a measurement mode switch from the second measurement mode to the first measurement mode;
determine a time point of completion of the measurement mode switch from the second measurement mode to the first measurement mode, and obtain a first impedance based on a first voltage obtained by the voltmeter immediately after the completion of the measurement mode switch from the second measurement mode to the first measurement mode; and
obtain a bioelectrical impedance of the object based on the first impedance and the second impedance.

11. The apparatus of claim 10, wherein a four-point impedance measurement method is used in the first measurement mode, and a two-point impedance measurement method is used in the second measurement mode.

12. The apparatus of claim 10, wherein the measurement mode switcher is further configured to switch the measurement mode from the second measurement mode to the first measurement mode by using the first switch to open the first electrode and the third electrode, which are short-circuited to each other in the second measurement mode, and by using the second switch to open the second electrode and the fourth electrode, which are short-circuited to each other in the second measurement mode.

13. The apparatus of claim 10, wherein the processor is further configured to generate the measurement mode switch signal in response to determining that the second impedance of the second measurement mode is less than a predetermined second threshold.

14. The apparatus of claim 10, wherein the processor is further configured to determine the time point of the completion of the measurement mode switch from the second measurement mode to the first measurement mode by monitoring a measurement impedance based on the voltage obtained by the voltmeter after the start of the measurement mode switch from the second measurement mode to the first measurement mode.

15. The apparatus of claim 14, wherein the processor is further configured to determine a time point at which a change of the measurement impedance turns from negative (−) to positive (+) as the time point of the completion of the measurement mode switch from the second measurement mode to the first measurement mode.

16. A method of measuring a bioelectrical impedance, by using an apparatus comprising a first electrode, a second electrode, a third electrode, a fourth electrode, a processor, and a measurement mode switcher, the method comprising:
obtaining, by the processor, a first impedance based on a first voltage of an object obtained immediately before start of a measurement mode switch from a first measurement mode to a second measurement mode;
switching, by the measurement mode switcher comprising a first switch between the first electrode and the third electrode and a second switch between the second electrode and the fourth electrode, a measurement mode from the first measurement mode to the second measurement mode by controlling the first switch and the second switch;
determining, by the processor, a time point of completion of the measurement mode switch from the first measurement mode to the second measurement mode, and obtaining a second impedance based on a second voltage of the object obtained immediately after the completion of the measurement mode switch from the first measurement mode to the second measurement mode; and
obtaining, by the processor, a bioelectrical impedance of the object based on the first impedance and the second impedance.

17. The method of claim 16, wherein a four-point impedance measurement method based on the first electrode, the second electrode, the third electrode, and the fourth electrode is used in the first measurement mode, and a two-point impedance measurement method based on the third electrode and the fourth electrode is used in the second measurement mode.

18. The method of claim 17, wherein the switching comprises switching the measurement mode from the first measurement mode to the second measurement mode by short-circuiting the first electrode and the third electrode to each other by using the first switch and short-circuiting the second electrode and the fourth electrode to each other by using the second switch.

19. The method of claim 16, wherein the switching comprises switching the measurement mode from the first measurement mode to the second measurement mode in response to determining that a predetermined period of time elapses in the first measurement mode and/or that the first impedance of the first measurement mode exceeds a predetermined first threshold.

20. The method of claim 16, wherein the obtaining the second impedance comprises determining a time point of the completion the measurement mode switch from the first measurement mode to the second measurement mode by monitoring measurement impedance based on a voltage obtained after the start of the measurement mode switch from the first measurement mode to the second measurement mode.

21. The method of claim 20, wherein the determining the time point of the completion of the measurement mode switch comprises determining a time point at which a change of the measurement impedance turns from positive (+) to negative (−) as the time point of the completion of the measurement mode switch from the first measurement mode to the second measurement mode.

22. The method of claim 16, further comprising:
repeatedly performing operations of obtaining the first impedance, switching from the first measurement mode to the second measurement mode, obtaining the second impedance, and obtaining the bioelectrical impedance until a difference between a currently obtained bioelectrical impedance and a bioelectrical impedance obtained immediately before the currently obtained bioelectrical impedance becomes equal to or less than a predetermined threshold.

23. An apparatus for measuring biometric information, the apparatus comprising:
a bioelectrical impedance measurer configured to obtain an bioelectrical impedance of an object, and
a biometric information estimator configured to estimate biometric information of the object based on the obtained bioelectrical impedance of the object,
wherein the bioelectrical impedance measurer comprises:
a first electrode,
a second electrode,
a third electrode,
a fourth electrode,
a current source configured to apply a constant current to the object through the first electrode and the second electrode;
a measurement mode switcher comprising a first switch between the first electrode and the third electrode and a second switch between the second electrode and the fourth electrode: the measurement mode switcher being configured to switch a measurement mode from a first measurement mode to a second measurement mode by controlling the first switch and the second switch in response to a measurement mode switch signal;
a voltmeter configured to obtain a voltage applied to the third electrode and the fourth electrode due to the constant current applied to the object through the first electrode and the second electrode, in the first measurement mode and the second measurement mode, respectively; and
a processor configured to:
obtain first impedance based on a first voltage obtained by the voltmeter immediately before start of a measurement mode switch from the first measurement mode to the second measurement mode;
determine a time point of completion of the measurement mode switch from the first measurement mode to the second measurement mode, and obtain a second impedance based on a second voltage measured immediately after completion of the measurement mode switch from the first measurement mode to the second measurement mode; and
obtain the bioelectrical impedance of the object based on the first impedance and the second impedance.

24. The apparatus of claim 23, wherein the biometric information comprises at least one of a body fat percentage, a body fat mass, a muscle mass, a skeletal muscle mass, a basal metabolic rate, an intracellular water content, an extracellular water content, a body water content, an inorganic mass, and a visceral fat content.

25. The apparatus of claim 23, wherein the biometric information estimator is further configured to estimate the biometric information by using a formula which defines a relationship between the bioelectrical impedance of the object and the biometric information of the object.

* * * * *